United States Patent
Maguire

(10) Patent No.: US 10,786,495 B2
(45) Date of Patent: Sep. 29, 2020

(54) VESICULAR MONOAMINE TRANSPORTER 2 INHIBITORS FOR TREATING STUTTERING

(71) Applicant: The Regents of the University of California, Oakland, CA (US)

(72) Inventor: Gerald A. Maguire, Riverside, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/157,007

(22) Filed: Oct. 10, 2018

(65) Prior Publication Data

US 2019/0105319 A1 Apr. 11, 2019

Related U.S. Application Data

(60) Provisional application No. 62/570,607, filed on Oct. 10, 2017.

(51) Int. Cl.
*A61K 31/4745* (2006.01)
*A61P 25/00* (2006.01)

(52) U.S. Cl.
CPC .......... *A61K 31/4745* (2013.01); *A61P 25/00* (2018.01)

(58) Field of Classification Search
CPC ............................. A61K 31/4745; A61P 25/00
See application file for complete search history.

(56) References Cited

U.S. PATENT DOCUMENTS 8,524,733 B2 * 9/2013 Gant .................... C07D 455/06
514/294

FOREIGN PATENT DOCUMENTS

WO WO-2015058053 A1 * 4/2015 ............. A61K 31/55

OTHER PUBLICATIONS

Austedo [deutetrabenazine] (Apr. 2017). Package Insert. Teva Pharmaceuticals USA, Inc., North Wales, PA.
Ingrezza [valbenazine] (Apr. 2017). Package Insert. Neurocrine Biosciences, Inc., San Diego, CA.
Hoang et al., (2015). "Case Report of Aripiprazole in the Treatment of Adolescent Stuttering," Annals Clin Psychiatry, 27:e1-e2.
Jankovic et al., (2016). "Deutetrabenazine in Tics Associated with Tourette Syndrome," Tremor and Other Hyperkinetic Movements, 6, 8 pages.
Maguire et al., (2000). "Risperidone for the Treatment of Stuttering," J Clinical Psychopharmacol, 20:479-482.
Maguire et al., (2002). "A Neurological Basis of Stuttering?" Lancet Neurol, 1:407.
Maguire et al., (2004). "Olanzapine in the Treatment of Developmental Stuttering: A Double-Blind, Placebo-Controlled Trial," Annals Clin Psychiatry, 16:63-72.
Maguire et al., (2004). "Alleviating Stuttering with Pharmacological Interventions," Expert Opinion Pharmacotherapy, 5:1565-1571.
Maguire et al., (2010). "Exploratory Randomized Clinical Study of Pagoclone in Persistent Developmental Stuttering: The Examining Pagoclone for Persistent Developmental Stuttering Study," J Clin Psychopharmacol, 30:48-56.
Maguire et al., (2012). "Overview of the Diagnosis and Treatment of Stuttering," J Exp Clin Med, 4:92-97.
Metzger et al., (2017). "Shifted Dynamic Interactions Between Subcortical Nuclei and Inferior Frontal Gyri During Response Preparation in Persistent Developmental Stuttering," Brain Struct Funct, 18 pages.
Wu et al., (1977). "Increased Dopamine Activity Associated with Stuttering," Neuroreport, 8:767-770.
Xenazine (tetrabenazine) (Sep. 2017). Package Insert. Recipharm Fontaine SAS, Fontaine-les-Dijon, France.

* cited by examiner

*Primary Examiner* — Sarah Pihonak
(74) *Attorney, Agent, or Firm* — Morrison & Foerster LLP

(57) ABSTRACT

Provided herein are pharmaceutical compositions comprising a vesicular monoamine transporter 2 (VMAT2) inhibitor (e.g., deutetrabenazine) and an excipient useful for treating stuttering in a subject in need thereof. Further provided are methods of treating stuttering in a subject in need thereof comprising administering an effective amount of a pharmaceutical composition of the present disclosure. Also provided herein are kits comprising such pharmaceutical compositions.

16 Claims, No Drawings

VESICULAR MONOAMINE TRANSPORTER 2 INHIBITORS FOR TREATING STUTTERING

CROSS-REFERENCE TO RELATED APPLICATIONS

This application claims benefit of U.S. Provisional Application No. 62/570,607, filed Oct. 10, 2017, which is incorporated by reference in its entirety.

FIELD OF THE INVENTION

The present disclosure relates to the use of a pharmaceutical composition comprising a vesicular monoamine transporter 2 (VMAT2) inhibitor for treating stuttering, and to kits comprising such compositions.

BACKGROUND

Stuttering is a chronic neuropsychiatric disorder that affects one percent of the population. Stuttering begins in childhood and persists, in most cases, throughout the lifetime. Spontaneous recovery can occur in younger children but by the age of eight years, if still present, the symptoms tend to continue through adulthood. Stuttering, also known as Childhood Onset Fluency Disorder, is a DSM-V Axis I condition that can greatly impact an individual's social, occupational and academic functioning. Unfortunately, current forms of speech therapy are associated with relatively low response rates and high rates of relapse.

Much has been learned in recent years of the neurophysiology of stuttering. In some instances, stuttering has been found to be amenable to pharmacologic treatment (Maguire et al., *J Clin Psychopharmacol*, 20:479-482, 2000; Maguire et al., *Annals Clin Psychiatry*, 16:63-72, 004; and Maguire et al., *Expert Opinion Pharmacotherapy*, 5:1565-1571, 2004). A past Phase IIb trial of pagoclone in the treatment of stuttering enrolled over 330 subjects in just two weeks with no formalized advertising for the trial. Such rapid enrollment for a stuttering medication study provides strong evidence for this population's need for more advanced treatment options (Maguire et al., *J Clin Psychopharmacol*, 30:48-56, 2010).

BRIEF SUMMARY

To meet the above and other needs, disclosed herein are pharmaceutical compositions comprising a vesicular monoamine transporter 2 (VMAT2) inhibitor useful for treating stuttering in patients in need thereof; methods comprising administering such pharmaceutical compositions to provide relief of one or more signs or symptoms of stuttering; and kits comprising such pharmaceutical compositions.

Accordingly, in one aspect, provided herein is a method of treating stuttering in a human subject in need thereof, the method comprising administering to the subject a pharmaceutical composition comprising an excipient and an effective amount of a vesicular monoamine transporter 2 (VMAT2) inhibitor to treat stuttering. In some embodiments, the VMAT2 inhibitor is deutetrabenazine, tetrabenazine, or valbenazine. In some embodiments, the VMAT2 inhibitor is deutetrabenazine.

In some embodiments that may be combined with any of the preceding embodiments, the subject has been diagnosed with childhood onset fluency disorder. In some embodiments, the subject does not have Huntington's disease. In some embodiments, the subject is from 8 to 60 years of age. In some embodiments, the subject is not currently taking a monoamine oxidase inhibitor or reserpine.

In some embodiments that may be combined with any of the preceding embodiments, a first dose of between 6 and 24 mg of the VMAT2 inhibitor is administered to the subject once per day. In some embodiments, the first dose is 12 mg/day of the VMAT2 inhibitor. In some embodiments, the first dose is 24 mg/day of the VMAT2 inhibitor. In some embodiments, a second dose of between 6 and 24 mg of the VMAT2 inhibitor is administered to the subject once per day. In some embodiments, the second dose is 12 mg/day of the VMAT2 inhibitor. In some embodiments, the second dose is 24 mg/day of the VMAT2 inhibitor. In some embodiments, no more than 48 mg of the VMAT2 inhibitor is administered to the subject each day.

In some embodiments that may be combined with any of the preceding embodiments, treating stuttering provides relief from one or more signs or symptoms of stuttering selected from facial tics, lip tremors, excessive eye blinking, tension in the face, frustration when attempting to communicate, hesitation before beginning to speak, brief silence before uttering a word, pauses within a word, refusal to speak, interjections of an extra sound into a sentence, repetition of a sound, tension in the voice, rearrangement of words in a sentence, prolonging a word, prolonging sounds within a word, and/or difficulty starting a word. In some embodiments, assessment of relief of the one or more signs or symptoms of stuttering is measured using a method selected from the group consisting of Stuttering Severity Instrument, Fourth Edition (SSI-IV), Overall Assessment of the Speaker's Experience of Stuttering (OAESES), and Subjective Screening of Stuttering Severity (SSS).

In another aspect, the present disclosure relates to an article of manufacture or kit comprising a pharmaceutical composition comprising an excipient and an effective amount of a VMAT2 inhibitor to treat stuttering, and a package insert comprising instructions for administering the pharmaceutical composition to a human subject suffering from one of more signs or symptoms of stuttering. In some embodiments, the VMAT2 inhibitor is deutetrabenazine, tetrabenazine, or valbenazine. In some embodiments, the VMAT2 inhibitor is deutetrabenazine. In some embodiments, the one or more signs or symptoms of stuttering are selected from the group consisting of facial tics, lip tremors, excessive eye blinking, tension in the face, frustration when attempting to communicate, hesitation before beginning to speak, brief silence before uttering a word, pauses within a word, refusal to speak, interjections of an extra sound into a sentence, repetition of a sound, tension in the voice, rearrangement of words in a sentence, prolonging a word, prolonging sounds within a word, and difficulty starting a word.

It is to be understood that one, some, or all of the properties of the various embodiments described above and herein may be combined to form other embodiments of the present disclosure. These and other aspects of the present disclosure will become apparent to one of skill in the art. These and other embodiments of the present disclosure are further described by the detailed description that follows.

DETAILED DESCRIPTION

Provided herein are pharmaceutical compositions comprising a vesicular monoamine transporter 2 (VMAT2) inhibitor (e.g., deutetrabenazine) and an excipient useful for treating stuttering in a subject in need thereof. Further provided are methods of treating stuttering in a human subject in need thereof comprising administering an effective amount of a pharmaceutical composition of the present disclosure. Also provided herein are kits comprising such pharmaceutical compositions.

As used herein and in the appended claims, the singular forms "a," "an," and "the" include plural references unless indicated otherwise. For example, "an" excipient includes one or more excipients.

The phrase "comprising" as used herein is open-ended, indicating that such embodiments may include additional elements. In contrast, the phrase "consisting of" is closed, indicating that such embodiments do not include additional elements (except for trace impurities). The phrase "consisting essentially of" is partially closed, indicating that such embodiments may further comprise elements that do not materially change the basic characteristics of such embodiments. It is understood that aspects and embodiments described herein as "comprising" include "consisting of" and "consisting essentially of" embodiments.

The term "about" as used herein in reference to a value, encompasses from 90% to 110% of that value (e.g., a dose of about 6 mg/day refers to a dose of 5.4 mg/day to 6.6 mg/day).

Pharmaceutical Compositions

Certain aspects of the present disclosure relate to pharmaceutical compositions comprising a vesicular monoamine transporter 2 (VMAT2) inhibitor and an excipient useful for treating stuttering in a human subject in need thereof.

In some embodiments, the pharmaceutical composition comprising a VMAT2 inhibitor. Any suitable VMAT2 inhibitor known in the art may be used in the pharmaceutical compositions and methods of the present disclosure, including, for example, deutetrabenazine, tetrabenazine, valbenazine, and any combinations thereof. In some embodiments, the pharmaceutical composition comprises one or more (e.g., one or more, two or more, or all three) of deutetrabenazine, tetrabenazine, and valbenazine. In some embodiments, the pharmaceutical composition comprises deutetrabenazine.

In some embodiments, the pharmaceutical compositions comprises between 1 and 48 mg of the VMAT2 inhibitor. For example, the pharmaceutical composition may comprise about 1 mg, about 2 mg, about 3 mg, about 4 mg, about 5 mg, about 6 mg, about 7 mg, about 8 mg, about 9 mg about 10 mg, about 11 mg, about 12 mg, about 13 mg, about 14 mg, about 15 mg, about 16 mg, about 17 mg, about 18 mg, about 19 mg, about 20 mg, about 21, mg about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, or about 48 mg of the VMAT2 inhibitor. In some embodiments, the pharmaceutical composition comprises between 6 and 24 mg of the VMAT2 inhibitor. In some embodiments, the pharmaceutical composition comprises about 6 mg of the VMAT2 inhibitor. In some embodiments, the pharmaceutical composition comprises about 12 mg of the VMAT2 inhibitor. In some embodiments, the pharmaceutical composition comprises about 24 mg of the VMAT2 inhibitor.

In some aspects, the present disclosure relates to a pharmaceutical composition comprising a VMAT2 inhibitor and an excipient. In some embodiments, the excipient comprises one or more of buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; polyols such as glycerol (e.g., formulations including 10% glycerol); salt-forming counter-ions such as sodium; metal complexes (e.g. Zn-protein complexes); and/or non-ionic surfactants such as polyethylene glycol (PEG). A thorough discussion of pharmaceutically acceptable carriers is available in REMINGTON'S PHARMACEUTICAL SCIENCES (Mack Pub. Co., N.J. 1991).

In some embodiments, the excipient further comprises one or more additional components. Examples of additional components may include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); wetting agents (e.g., sodium lauryl sulphate, etc.); salt solutions; alcohols; polyethylene glycols; gelatin; lactose; amylase; magnesium stearate; talc; silicic acid; viscous paraffin; hydroxymethylcellulose; polyvinylpyrrolidone; perfuming agents; colorants; flavorants moisturizers; sunscreens; and the like.

In some embodiments, the excipient/pharmaceutical composition is adapted for oral administration.

Pharmaceutical compositions and formulations of the present disclosure may be prepared by mixing the VMAT2 inhibitor with one or more excipients. Pharmaceutical compositions/formulations to be used for in vivo administration are generally sterile. Sterility may be readily accomplished, e.g., by filtration through sterile filtration membranes.

Methods

Certain aspects of the present disclosure relate to methods of treating stuttering in a subject in need thereof comprising administering a pharmaceutical composition described herein to treat stuttering. In some embodiments, the methods described herein provide relief from one or more signs or symptoms of stuttering. In some embodiments, the pharmaceutical composition is administered orally.

In some embodiments, the subject is a human. In some embodiments, the subject has been diagnosed with childhood onset fluency disorder. In some embodiments, the subject is suspected of having childhood onset fluency disorder. In some embodiments, the subject is at risk of developing childhood onset fluency disorder. In some embodiments, the subject is at least 8 years of age. In some embodiments, the subject is between 8 and 60 years of age. In some embodiments, the subject is at least 18 years of age. In some embodiments, the subject is between 18 and 60 years of age. In some embodiments, the subject does not have Huntington's disease. In some embodiments, the subject is not currently taking on or more of antipsychotics, metoclopramide, monoamine oxidase inhibitors, levodopa or dopamine agonists, reserpine, amantadine, and/or memantine. In some embodiments, the subject is not currently taking a monoamine oxidase inhibitor and/or reserpine.

In some embodiments, the subject is administered one or more (e.g., one or more, two or more, etc.) doses of a pharmaceutical composition of the present disclosure. In some embodiments, the subject is administered a first dose of a pharmaceutical composition described herein once per day. In some embodiments, the subject is administered a first dose comprising between 6 and 24 mg of a VMAT2 inhibitor once per day. For example, the first dose may comprise about 6 mg, about 7 mg, about 8 mg, about 9, mg about 10 mg, about 11 mg, about 12 mg, about 13 mg, about 14 mg, about 15 mg, about 16 mg, about 17 mg, about 18 mg, about 19 mg, about 20 mg, about 21, mg about 22 mg, about 23 mg, or about 24 mg of the VMAT2 inhibitor. In some embodiments, the first dose comprises about 6 mg/day of the VMAT2 inhibitor. In some embodiments, the first dose comprises about 9 mg/day of the VMAT2 inhibitor. In some embodiments, the first dose comprises about 12 mg/day of the VMAT2 inhibitor. In some embodiments, the first dose comprises 24 mg/day of the VMAT2 inhibitor. In some embodiments, the first dose is administered to the subject in the morning.

In some embodiments, the subject is administered a second dose of a pharmaceutical composition described herein once per day. In some embodiments, the subject is administered a second dose comprising between 6 and 24 mg of a VMAT2 inhibitor once per day. For example, the second dose may comprise about 6 mg, about 7 mg, about 8 mg, about 9, mg about 10 mg, about 11 mg, about 12 mg, about 13 mg, about 14 mg, about 15 mg, about 16 mg, about 17 mg, about 18 mg, about 19 mg, about 20 mg, about 21, mg about 22 mg, about 23 mg, or about 24 mg of the VMAT2 inhibitor. In some embodiments, the second dose comprises about 6 mg/day of the VMAT2 inhibitor. In some embodiments, the second dose comprises about 9 mg/day of the VMAT2 inhibitor. In some embodiments, the second dose comprises about 12 mg/day of the VMAT2 inhibitor. In some embodiments, the second dose comprises 24 mg/day of the VMAT2 inhibitor. In some embodiments, the second dose is administered to the subject in the evening.

In some embodiments, the subject is administered a first and second dose of a pharmaceutical composition of the present disclosure, where the first and second doses comprise the same amount of the VMAT2 inhibitor. In some embodiments, the first and second doses each comprise about 6 mg of the VMAT2 inhibitor. In some embodiments, the first and second doses each comprise about 9 mg of the VMAT2 inhibitor. In some embodiments, the first and second doses each comprise about 12 mg of the VMAT2 inhibitor. In some embodiments, the first and second doses each comprise about 24 mg of the VMAT2 inhibitor. In some embodiments, the first dose is administered to the subject in the morning, and the second dose is administered to the subject in the evening.

In some embodiments, the subject is administered a first and second dose of a pharmaceutical composition of the present disclosure, where the first and second doses comprise different amounts of the VMAT2 inhibitor. In some embodiments, the first dose comprises more of the VMAT2 inhibitor than the second dose. In some embodiments, the first dose comprises less of the VMAT2 inhibitor than the second dose. In some embodiments, the first dose comprises about 12 mg of the VMAT2 inhibitor and the second dose comprises about 24 mg of the VMAT2 inhibitor. In some embodiments, the first dose is administered to the subject in the morning, and the second dose is administered to the subject in the evening.

In some embodiments, no more than 48 mg of the VMAT2 inhibitor is administered to the subject each day.

In some embodiments, a pharmaceutical composition of the present disclosure is administered for one, two, three, four, five, six, seven or more consecutive days. In some embodiments, a pharmaceutical composition of the present disclosure is administered for one, two, three, four, five, six, seven, eight, nine, 10, 11, 12 or more consecutive weeks. In some embodiments, a pharmaceutical composition of the present disclosure is administered for one, two, three, four, five, six, seven, eight, nine, 10, 11, 12 or more consecutive months. In some embodiments, a pharmaceutical composition do the present disclosure is administered for one year or more.

In some embodiments, the methods described herein provide relief from one or more signs or symptoms of stuttering in the subject. In some embodiments, the signs or symptoms of stuttering are one or more (e.g., one or more, two or more, three or more, four or more, five or more, etc.) of facial tics, lip tremors, excessive eye blinking, tension in the face, frustration when attempting to communicate, hesitation before beginning to speak, brief silence before uttering a word, pauses within a word, refusal to speak, interjections of an extra sound into a sentence, repetition of a sound, tension in the voice, rearrangement of words in a sentence, prolonging a word, prolonging sounds within a word, and difficulty starting a word.

In some embodiments, relief of the one or more signs or symptoms of stuttering comprises a measurable improvement in the one or more signs or symptoms. In some embodiments, the improvement is self-reported by the subject. In some embodiments, the improvement is observed and/or reported by a health care professional. Relief of one or more signs or symptoms of stuttering may be measured (e.g., by the subject, by a health care professional etc.) using any suitable assay or method known in the art, including, for example, using a method such as the Stuttering Severity Instrument, Fourth Edition (SSI-IV), Overall Assessment of the Speaker's Experience of Stuttering (OAESES), and Subjective Screening of Stuttering Severity (SSS).

Article of Manufacture of Kit

Certain aspects of the present disclosure relate to an article of manufacture or kit comprising a pharmaceutical composition comprising an excipient and an effective amount of a VMAT2 inhibitor. In some embodiments, the VMAT2 inhibitor is one or more of deutetrabenazine, tetrabenazine, valbenazine, and any combinations thereof. In some embodiments, the VMAT2 inhibitor is deutetrabenazine. In some embodiments, the article of manufacture or kit comprises a label and/or package insert comprising instructions for use of the pharmaceutical composition. In some embodiments, the pharmaceutical composition is provided in a container. In some embodiments, the components of the pharmaceutical composition are provided in a single container, or in two or more separate containers. In some embodiments, the article of manufacture or kit comprises the container(s) and a label or package insert on or associated with the container(s). Suitable containers may include, for example, bottles, vials, bags, etc. The container may be formed from a variety of suitable materials such as glass, plastic (such as polyvinyl chloride or polyolefin), metal, and/or metal alloy (such as stainless steel). The article of manufacture or kit may further include other materials desirable from a commercial and user standpoint, including buffers, diluents, filters, syringes, applicators, and the like.

The foregoing written description is considered to be sufficient to enable one skilled in the art to practice the present disclosure. The following Examples are offered for illustrative purposes only, and are not intended to limit the scope of the present disclosure in any way. Indeed, various modifications of the present disclosure in addition to those shown and described herein will become apparent to those skilled in the art from the foregoing description and fall within the scope of the appended claims.

EXAMPLES

Example 1: Deutetrabenazine for the Treatment of Stuttering

Stuttering is considered to be a disorder of the central nervous system. Early research suggests that stuttering is associated with low metabolic function of the striatum secondary to a hyperdopaminergic state and with elevated cerebral dopamine levels (Wu et al., *Neuroreport*, 8:767-70, 1997). This example describes an open label study of deutetrabenazine in adult subjects (18-60 years of age) who are moderate to severe stutterers based on CGI-S and SSI-IV.

The primary objective of this study is to evaluate the efficacy and tolerability of deutetrabenazine in reducing one or more signs or symptoms of stuttering. This is a single-center, open label study investigating the use of deutetrabenazine in adults (ages 18-60 years) who suffer from developmental stuttering. The following scales are used to determine clinical outcomes: Stuttering Severity Instrument, Fourth Edition (SSI-IV); Clinical Global Impression Scale-Severity Investigator (CGI-S: Investigator) and Patient (CGI-S: Patient); Subjective Screening of Stuttering Severity (SSS); and Overall Assessment of the Speaker's Experience of Stuttering (OASES). Speech samples are collected and fluency is measured using the objective stuttering measurement (SSI-IV) utilizing a conversation and reading task. The subject speaks to another individual for approximately 10 minutes in a structured conversation, and also reads a magazine article or non-emotional content aloud. The clinical outcome measure is video/audio recorded to measure change and rating accuracy. Each subject completes a participant questionnaire that concerns their stuttering (SSS and OASES). Subjects are enrolled in the study if they meet the following criteria: the subject satisfies DSM-V criteria for childhood onset fluency disorder (stuttering); the nature of stuttering is developmental in origin with the onset prior to ten years of age; the subject has a score of moderate or higher on the SSI-IV; the subject is male or female from ages 18-60; and the subject has a MADRS total score of f≤13 (Normal Mood). Subjects are excluded from the study if: the subject has a serious untreated or under-treated psychiatric illness, such as depression, at Screening or Baseline; the subject has active suicidal ideation at screening or baseline; the subject has an unstable or serious medical or psychiatric illness at screening or baseline; the subject has been recently exposed to tetrabenazine; the subject has received any of the following concomitant medications within 30 days of screening or baseline: antipsychotics, metoclopramide, monoamine oxidase inhibitors (MAOI), levodopa or dopamine agonists, reserpine, or amantadine, memantine; or the subject has Parkinson's disease, dementia, or other degenerative neurologic illness.

Subjects are tested for extrapyramidal, Tardive Dyskinesia side effects and suicidality using the Columbia-Suicide Severity Rating Scale (C-SSRS), Montgomery Asberg Depression rating scale (MADRS), Simpson-Angus Scale (SAS), Barnes Akathisia Scale(BARS), and Abnormal Involuntary Movement Scale (AIMS). At Visit 2 (Day 0), subjects are dispensed 12 mg deutetrabenazine once a day for two weeks. At visit 3 (day 14), subjects are dispensed 12 mg deutetrabenazine tablets, one tablet twice a day for the following two weeks. At Visit 4 (Day28), subjects are dispensed 12 mg tablets, one tablet in the morning and two at night for the following two weeks. At Visit 5 (Day 42), subjects are dispensed 12 mg tablets, two tablets twice a day for the remainder of the treatment phase. If there is deemed improvement by the investigator, the subject remains on the same dose. If there is no improvement, then the subject's dose is increased to the maximum of 24 mg twice a day. If the subject does not tolerate the increase in medication, the dose can is reduced, in consultation with the treating physician, back down to the previous dose. At each visit, the following assessments are performed: vital signs including body weight, sitting blood pressure, pulse, and temperature are taken; MADRS; C-SSRS; Clinical Global Impression Scale-Severity Investigator Rating; Clinical Global Impression Scale-Severity Patient Rating; Clinical Global Impression Scale-Improvement Investigator Rating; Clinical Global Impression Scale-Improvement Patient Rating; Subject-rated OASES; Subject-rated SSS; Stuttering Severity Instrument, Fourth Edition (SSI-IV); labs: blood (and urine for pregnancy if indicated); physical examination; concomitant medications collected and recorded; dispense drugs; and return drug/accountability. At each visit an assessment of an individual's side-effects, possible Adverse Events, is gathered by the physician. Furthermore, all adverse events are recorded.

The primary endpoints will be the total SSI-IV score. Furthermore, a patient rated scale, the SSS, will also be considered to be a primary efficacy endpoint as well. The CGI (I and S) and OASES will serve as secondary endpoints.

Other secondary endpoints will be the tolerability scales (i.e. Simpson Angus Scale [SAS], Barnes Akathisia Scale [BARS], and the Abnormal Involuntary Movement Scale [AIMS]) as well as any changes in laboratory values.

What is claimed is:

1. A method of treating stuttering in a human subject in need thereof, the method comprising administering to the subject a pharmaceutical composition comprising an excipient and an effective amount of a vesicular monoamine transporter 2 (VMAT2) inhibitor to treat stuttering, wherein the VMAT2 inhibitor is selected from the group consisting of deutetrabenazine, tetrabenazine, and valbenazine, and wherein the VMAT2 inhibitor is the only active agent administered to treat stuttering.

2. The method of claim 1, wherein the VMAT2 inhibitor is deutetrabenazine.

3. The method of claim 1, wherein the subject has been diagnosed with childhood onset fluency disorder.

4. The method of claim 3, wherein the subject does not have Huntington's disease.

5. The method of claim 3, wherein the subject is from 8 to 60 years of age.

6. The method of claim 3, wherein the subject is not currently taking a monoamine oxidase inhibitor or reserpine.

7. The method of claim 3, wherein a first dose of between about 6 mg and about 24 mg of the VMAT2 inhibitor is administered to the subject once per day.

8. The method of claim 7, wherein the first dose is about 12 mg/day of the VMAT2 inhibitor.

9. The method of claim 7, wherein the first dose is about 24 mg/day of the VMAT2 inhibitor.

10. The method of claim 7, wherein a second dose of between about 6 mg and about 24 mg of the VMAT2 inhibitor is administered to the subject once per day.

11. The method of claim 10, wherein the second dose is about 12 mg/day of the VMAT2 inhibitor.

12. The method of claim 10, wherein the second dose is about 24 mg/day of the VMAT2 inhibitor.

13. The method of claim 3, wherein no more than 48 mg of the VMAT2 inhibitor is administered to the subject each day.

14. The method of claim 3, wherein treating stuttering provides relief from one or more signs or symptoms of stuttering selected from the group consisting of facial tics, lip tremors, excessive eye blinking, tension in the face, frustration when attempting to communicate, hesitation before beginning to speak, brief silence before uttering a word, pauses within a word, refusal to speak, interjections of an extra sound into a sentence, repetition of a sound, tension in the voice, rearrangement of words in a sentence, prolonging a word, prolonging sounds within a word, and difficulty starting a word.

15. The method of claim 14, wherein assessment of relief of the one or more signs or symptoms of stuttering is measured using a method selected from the group consisting of Stuttering Severity Instrument, Fourth Edition (SSI-IV), Overall Assessment of the Speaker's Experience of Stuttering (OAESES), and Subjective Screening of Stuttering Severity (SSS).

16. The method of claim 1, wherein the subject is not currently taking a dopamine agonist.

* * * * *